United States Patent [19]

Knifton

[11] 4,332,914

[45] Jun. 1, 1982

[54] MANUFACTURE OF ALKANOLS FROM SYNTHESIS GAS

[75] Inventor: John F. Knifton, Austin, Tex.

[73] Assignee: Texaco Inc., White Plains, N.Y.

[21] Appl. No.: 277,527

[22] Filed: Jun. 26, 1981

[51] Int. Cl.³ .............................................. C07C 27/06
[52] U.S. Cl. .................................... 518/700; 252/428; 252/430; 252/471; 252/472
[58] Field of Search ................................. 518/700, 715

[56] References Cited

U.S. PATENT DOCUMENTS 4,206,134  6/1980  Kugler et al. ...................... 518/715
4,265,828  5/1981  Knifton .............................. 518/700

Primary Examiner—Howard T. Mars
Attorney, Agent, or Firm—Carl G. Ries; Jack H. Park; Walter D. Hunter

[57] ABSTRACT

This invention concerns a process of making alkanols and particularly methanol which comprises the steps of contacting a mixture of CO and $H_2$ with a catalyst system comprising a ruthenium-containing compound and a halogen-free rhenium-containing compound or a halogen-free manganese-containing compound dispersed in a low melting quaternary phosphonium base or salt, and heating said resultant reaction mixture under a pressure of 500 psig or greater at a temperature of at least 150° C.

23 Claims, No Drawings

MANUFACTURE OF ALKANOLS FROM SYNTHESIS GAS

BACKGROUND OF THE INVENTION

1. Field of the Invention

This invention concerns an improved process for preparing alkanols and especially alkanols rich in methanol by reaction of oxides of carbon with hydrogen in presence of a catalyst system.

Prior Art

It has long been known that monofunctional alcohols such as methanol, ethanol, etc. can be formed by the reaction of synthesis gas, i.e., a mixture of carbon monoxide and hydrogen at elevated pressures of, for example, up to 1000 atmospheres, and at temperatures of from about 200° to 500° C. or more using as a catalyst a mixture of copper, chromium and zinc oxides. A wide variety of other catalysts have been employed in the reaction of carbon monoxide and hydrogen to yield liquid products containing substantial amounts of monofunctional alcohols as exemplified by methanol, ethanol, propanol, etc. For example, in U.S. Pat. No. 4,013,700 the reaction of carbon monoxide and hydrogen in the presence of a quaternary phosphonium cation and a rhodium carbonyl complex yields a liquid product having a high methanol content. In U.S. Pat. No. 4,014,913 where the same reactants are contacted with a solid catalyst comprising a combination of rhodium and manganese the product formed contains substantial amounts of ethanol and in U.S. Pat. No. 4,197,253 where the reaction of carbon monoxide and hydrogen is conducted in the presence of a rhodium carbonyl complex and a phosphine oxide compound the resulting product contains a high concentration of methanol. Likewise, when the same reactants are contacted with a rhodium carbonyl complex and a copper salt a liquid product containing a substantial amount of methanol is formed.

One serious problem associated with synthesis gas operations in the past has been the non-selectivity of the product distribution since high activity catalysts generally yield a liquid product containing numerous hydrocarbon materials. Thus, complicated recovery schemes are necessary to separate the desired products and the overall yield of the valuable organic products is low. This is a definite need in the art for a process which will produce alkanols and especially methanol-rich alkanols with a high degree of selectivity from synthesis gas.

This invention therefore is to provide a process of making alkanols by resort to a unique catalyst system which produces said alkanols in good yields and with excellent selectivity especially with regard to methanol formation.

SUMMARY OF THE INVENTION

This invention concerns a method for making methanol-rich alkanols which comprises contacting a mixture of CO and $H_2$ at a pressure of 500 psig or higher and at a temperature of at least 150° C. with a catalyst system composed of a ruthenium-containing compound and a halogen-free rhenium-containing compound or a halogen-free manganese-containing compound dispersed in a low melting quaternary phosphonium base or salt. Surprisingly, with the process of this invention, selectivities for methanol as high as 85 percent have been achieved and amounts of $C_1$ and $C_2$ alkanols in the liquid product of up to 95 weight percent have been obtained.

DETAILED DESCRIPTION OF THE INVENTION

In the narrower and more preferred practice of this invention, alkanols such as methanol, ethanol, etc. are prepared by contacting a mixture of carbon monoxide and hydrogen at a temperature of about 180° to about 250° C. and at a pressure of 2000 psig or greater with a catalyst system comprising a ruthenium-containing compound and a halogen-free rhenium-containing compound or a halogen-free manganese-containing compound dispersed in a low melting quaternary phosphonium base or salt.

If desired, in practicing this invention, mixtures of the ruthenium, rhenium or manganese-containing compounds may be employed.

The ruthenium-containing compounds, the halogen-free rhenium-containing compounds and the halogen-free manganese-containing compounds utilized as catalysts in the process of this invention may be chosen from a wide variety of organic or inorganic compounds, complexes, etc., as will be shown and illustrated below. It is only necessary that the catalyst precursors actually employed contain the said metal in any of their ionic states. The actual catalytically active species is then believed to comprise ruthenium, rhenium or manganese in complex combination with carbon monoxide and hydrogen. The most effective catalysis is believed to be achieved where ruthenium, rhenium or manganese hydrocarbonyl species are solubilized in a quaternary salt under reaction conditions.

The ruthenium-containing compounds employed as a catalyst may take many different forms. For instance, the ruthenium may be added to the reaction mixture in an oxide form, as in the case of, for example, ruthenium(IV) oxide hydrate, anhydrous ruthenium(IV) dioxide and ruthenium(VIII) tetraoxide. Alternatively, it may be added as the salt of a mineral acid, as in the case of ruthenium(III) chloride hydrate, ruthenium(III) bromide, ruthenium(III) triiodide, tricarbonyl ruthenium nitrate, or as the salt of a suitable organic carboxylic acid, for example, ruthenium(III) acetate, ruthenium naphthenate, ruthenium valerate and ruthenium complexes with carbonyl-containing ligands such as ruthenium(III) acetylacetonate. The ruthenium may also be added to the reaction zone as a carbonyl or hydrocarbonyl derivative. Here, suitable examples include triruthenium dodecacarbonyl and other hydrocarbonyls such as $H_2Ru_4(CO)_{13}$ and $H_4Ru_4(CO)_{12}$, and substituted carbonyl species such as the tricarbonylruthenium(II) chloride dimer, $[Ru(CO)_3Cl_2]_2$.

Preferred ruthenium-contaning compounds include oxides of ruthenium, ruthenium salts of an organic carboxylic acid and ruthenium carbonyl or hydrocarbonyl derivatives. Among these, particularly preferred are ruthenium(IV) dioxide hydrate, ruthenium(VIII) tetraoxide, anhydrous ruthenium(IV) oxide, ruthenium acetate, ruthenium(III) acetylacetonate, and triruthenium dodecacarbonyl.

The rhenium and manganese catalyst precursors may take many different forms. For instance, the rhenium or manganese may be added to the reaction mixture in an oxide form, as in the case of, for example, of manganese(II) oxide, manganese(III) oxide, manganese(IV) oxide, rhenium(IV) oxide, rhenium(VI) oxide and rhenium(VII) oxide. Alternatively, they may be added as halogen-free salts of a mineral acid, as in the case of manganese(II) nitrate and manganese(II) sulphate, as the salt of a suitable organic carboxylic acid, for example, manganese(II) acetate, manganese(III) acetate and manganese oxalate, or as the complex of a carbonyl-containing ligand, as in the case of manganese(II) acetylacetonate or manganese(III) acetylacetonate, etc. Manganese and rhenium carbide, carbonate carbonyl and hydrocarbonyl derivatives such as manganese carbide, manganese(II) carbonate, dimanganese decacarbonyl and dirhenium decacarbonyl are also effective catalyst precursors.

Preferred manganese and rhenium-containing compounds include carbonates such as manganese(II) carbonate, complexes of carbonyl-containing ligands such as manganese(III) acetylacetonate, manganese and rhenium carbonyls such as dimanganese decacarbonyl and dirhenium decacarbonyl, as well as salts of organic acids such as manganese(III) acetate.

The catalyst system of this invention is, prior to its catalytic use in making alkanols, first dispersed in a low melting quaternary phosphonium base or salt. It is interesting to note that the ruthenium-containing compound alone, without being dispersed in said salt or base, has little, if any activity in promoting the manufacture of alkanols from synthesis gas.

The quaternary phosphonium base or salt must be relatively low melting, that is, melt at a temperature less than about the temperature of reaction of making alkanols. Usually the quaternary compound employed has a melting point less than about 180° C. and preferably has a melting point less than 150° C.

Suitable quaternary phosphonium salts have the formula:

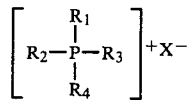

where $R_1$, $R_2$, $R_3$ and $R_4$ are organic radicals, particularly aryl or alkaryl radicals bonded to the phosphorous atom, and X is an anionic species. The organic radicals useful in this instance include those alkyl radicals having 1 to 20 carbon atoms in a branched or linear alkyl chain; they include the methyl, ethyl, n-butyl, iso-butyl, octyl, 2-ethylhexyl and dodecyl radicals. Tetraethylphosphonium bromide and tetrabutylphosphonium bromide are typical examples presently in commercial production. The corresponding quaternary phosphonium acetates, hydroxides, nitrates, chromates, tetrafluoroborates and other halides, such as the corresponding chlorides, and iodides, are also satisfactory in this instance.

Equally useful are the phosphonium salts containing phosphorus bonded to a mixture of alkyl, aryl and alkaryl radicals. Said alkyl and alkaryl radicals may each contain 6 to 20 carbon atoms. The aryl radicals may each contain 6 to 20 carbon atoms. The aryl radical is most commonly phenyl. The alkaryl group may comprise phenyl substituted with one or more $C_1$-$C_{10}$ alkyl substituents, bonded to the phosphorus atom through the aryl function.

Illustrative examples of suitable quaternary phosphonium bases and salts include tetrabutylphosphonium bromide, heptyltriphenylphosphonium bromide, tetrabutylphosphonium iodide, tetrabutylphosphonium chloride, tetrabutylphosphonium nitrate, tetrabutylphosphonium hydroxide, tetrabutylphosphonium chromate, tetrabutylphosphonium tetrafluoroborate, and tetrabutylphosphonium acetate.

Mixtures of any of the previously described quaternary bases or salts may be utilized in the process of this invention.

The preferred quaternary salts are generally the tetralkylphosphonium salts containing alkyl groups having one to six carbon atoms, such as methyl, ethyl, and butyl. Tetrabutylphosphonium salts, such as tetrabutylphosphonium bromide, are most preferred for the practice of this invention. Preferred tetrabutylphosphonium salts or bases include the bromide, chloride, iodide, acetate and chromate salts and hydroxide base.

Generally, in the catalyst system the molar ratio of the ruthenium compound to the quaternary phosphonium salt or base will range from about 1:0.01 to about 1:100 or more and, preferably, will be from about 1:0.5 to about 1:20.

The quantity of ruthenium and rhenium or manganese compounds employed in the instant invention is not critical and may vary over a wide range. In general, the novel process is desirably conducted in the presence of a catalytically effective quantity of the active ruthenium species and of the active rhenium species or manganese species which gives the desired product in reasonable yield. The reaction proceeds when employing as little as about $1 \times 10^{-6}$ weight percent, and even lesser amounts, of ruthenium together with about $1 \times 10^{-6}$ weight percent or less of rhenium or manganese, basis the total weight of the reaction mixture. The upper concentration is dictated by a variety of factors including catalyst cost, partial pressures of carbon monoxide and hydrogen, operating temperature, etc. A ruthenium concentration of from about $1 \times 10^{-5}$ to about 10 weight percent in conjunction with a rhenium or manganese concentration of from about $1 \times 10^{-5}$ to about 5 weight percent, based on the total weight of reaction mixture is generally desirable in the practice of this invention. The preferred ruthenium to manganese or rhenium atomic ratios are from 10:1 to 1:10.

The temperature range which can usefully be employed in these syntheses is a variable dependent upon other experimental factors, including the pressure, and the concentration and choice of the particular species of the ruthenium catalyst as well as the rhenium or manganese catalyst among other things. The range of operability is from about 150° to 350° C. when superatmospheric pressure of syngas are employed. A narrow range of 180°–250° C. represents the preferred temperature range.

Superatmospheric pressures of 500 psi or greater lead to substantial yields of alkanols by the process of this invention. A preferred operating range is from 2000 psig to 9000 psig, although pressures above 9000 psig also provide useful yields of the desired alkanols.

The relative amounts of carbon monoxide and hydrogen which may be initially present in the syngas, i.e., synthesis gas, mixture are variable, and these amounts may be varied over a wide range. In general, the mole ratio of $CO:H_2$ is in the range from about 20:1 up to about 1:20, preferable from about 5:1 to 1:5, although ratios outside these ranges may also be employed. Particularly in continuous operations, but also in batch experiments, the carbon monoxide-hydrogen gaseous mixtures may also be used in conjunction with up to 50 percent by volume of one or more other gases. These other gases may include one or more inert gases such as nitrogen, argon, neon and the like, or they may include gases that may, or may not, undergo reaction under CO hydrogenation conditions, such as carbon dioxide, hydrocarbons such as methane, ethane, propane and the like, ethers such as dimethyl ether, methylethyl ether and diethyl ether, alkanols such as methanol and acid esters such as methyl acetate.

Acetic acid esters such as methyl acetate, ethyl acetate, etc. may also be formed during the operation of the process of this invention such as methyl acetate, ethyl acetate and in some instances small amounts of esters of other monocarboxylic acids as well as acetaldehyde may be produced. The relative concentrations of methanol, ethanol, propanol, the acetic acid esters, etc. in the crude liquid product are set out in the examples for a variety of catalyst systems.

The novel process of this invention can be conducted in a batch, semi-continuous or continuous fashion. The catalyst may be initially introduced into the reaction zone batchwise, or it may be continuously or intermittently introduced into such a zone during the course of the synthesis reaction. Operating conditions can be adjusted to optimize the formation of the desired alkanol products, and said materials may be recovered by methods well known in the art, such as distillation, fractionation, extraction and the like. A fraction rich in the catalyst components may then be recycled to the reaction zone, if desired, and additional products generated.

The products have been identified in this work by one or more of the following analytical procedures, viz, gas-liquid phase chromatograph (glc), infrared (ir), mass spectrometry, nuclear magnetic resonance (nmr) and elemental analyses, or a combination of these techniques. Analyses have, for the most part, been by parts in weight; all temperatures are in degrees centigrade and all pressures in pounds per square inch gauge (psig).

The following examples illustrate various embodiments of this invention and are to be considered not limitative.

EXAMPLE 1

This Example illustrates the synthesis of methanol-rich alkanols catalyzed by ruthenium-plus-rhenium-containing compounds dispersed in tetrabutylphosphonium bromide salt (m.p. 100° C.).

A mixture of ruthenium(IV) oxide, hydrate (2 mmoles) and rhenium decacarbonyl (8 mmoles Re) dispersed in tetrabutylphosphonium bromide (10.0 g, 29.7 mmoles) was transferred in a glass liner under nitrogen purge to an 850 ml capacity pressure reactor equipped with heating and means of agitation. The reactor was sealed, flushed with a carbon monoxide-hydrogen mixture (1:1 molar) and pressured to 2000 psig with the same carbon monoxide-hydrogen. The mixture was heated to 220° C. with rocking, the pressure raised to 6350 psig with the carbon monoxide-hydrogen mixture from a large surge tank, and the reactor held at temperature for 6 hours. Pressure was maintained at ca. 6350 psig by incremental additions of the carbon monoxide-hydrogen mixture from the surge tank.

On cooling, the reactor pressure (3240 psig) was noted, a gas sample was taken and the excess gas removed. The red liquid product (23.9 g) was analyzed by glc and Karl Fisher titration and the following results were obtained:

84.7 wt. % methanol
9.4 wt. % ethanol
1.0 wt. % methyl formate
0.2 wt. % methyl formate
0.4 wt. % methyl acetate
0.3 wt. % ethyl acetate
4.0 wt. % unidentified
0.2 wt. % water The liquid yield increase was $(23.9-12.9/12.9) \times 100 = 85$ wt. %.

Turnover numbers, basis total $C_1+C_2$ alkanol produced, are ca. 160 mole/gram atom Ru.

The alkanol fractions were recovered from the crude liquid produced by distillation. The dark brown liquid residue resolidified upon cooling.

Analyses of typical off-gas samples showed the presence of:

38% hydrogen
12% carbon monoxide
1% methane
47% carbon monoxide

EXAMPLES 2-13

A number of additional examples were conducted in the same manner as Example 1. Data relating to these examples is presented in Table I. It may be noted that:

a. A number of combinations of ruthenium with both rhenium and manganese species when dispersed in tetrabutylphosphonium salt have been found to yield the desired alkanols.

b. General higher yields of desired alkanols were obtained when molar proportion of rhenium or manganese catalyst precursor exceeded that of the ruthenium component.

c. No alkanol product was detected in the absence of ruthenium, e.g., when starting with rhenium or manganese catalyst precursor alone.

TABLE I

| | METHANOL-RICH ALKANOLS FROM SYNGAS[a] | | | | | | | | | |
|---|---|---|---|---|---|---|---|---|---|---|
| | Catalyst | | LIQUID PRODUCT COMPOSITION (WT %)[d] | | | | | | | Liquid Yield |
| Example | Composition | Melt | MeOH | EtOH | PrOH | MeOAc | EtOAc | $CH_3CHO$ | $H_2O$ | Increase (Wt %) |
| 1 | $RuO_2$—$2Re_2(CO)_{10}$ | $Bu_4PBr$ | 84.7 | 9.4 | | 0.4 | 0.3 | | 0.7 | 85 |
| 2 | $RuO_2$—$2Re_2(CO)_{10}$ | $Bu_4PBr$[b] | 58.8 | 8.6 | 0.9 | | 0.3 | | 8.8 | 153 |
| 3 | $RuO_2$—$Re_2(CO)_{10}$ | $Bu_4PBr$[b] | 67.3 | 25.7 | 0.6 | 1.7 | 0.6 | | 1.0 | 168 |
| 4 | $RuO_2$—$Re_2(CO)_{10}$ | $Bu_4PBr$ | 80.5 | 9.5 | | 1.0 | 0.5 | | 0.9 | 90 |
| 5 | $2RuO_2$—$Re_2(CO)_{10}$ | $Bu_4PBr$[b] | 72.3 | 18.1 | 0.4 | 1.6 | 0.7 | | 1.7 | 164 |
| 6 | $2RuO_2$—$Re_2(CO)_{10}$ | $Bu_4PBr$[c] | 28.7 | 3.9 | 1.1 | 0.3 | | | 12.0 | 31 |
| 7 | $Re_2(CO)_{10}$ | $Bu_4PBr$[b] | — | — | — | — | — | — | — | 5 |
| 8 | $RuO_2$—$2Mn_2(CO)_{10}$ | $Bu_4PBr$[b] | 58.1 | 22.4 | 2.3 | 2.3 | 0.8 | 2.3 | 2.7 | 118 |
| 9 | $RuO_2$—$2Mn_2(CO)_{10}$ | $Bu_4PBr$ | 50.4 | 36.4 | 1.5 | 1.2 | 0.5 | 2.0 | 1.3 | 63 |
| 10 | $2RuO_2$—$Mn_2(CO)_{10}$ | $Bu_4PBr$[c] | 20.1 | 3.9 | 1.4 | 0.3 | | | 17.7 | 115 |
| 11 | $RuO_2$—$4Mn(AcAc)_3$ | $Bu_4PBr$ | 48.1 | 16.8 | 0.8 | 9.9 | 5.7 | | 1.4 | 44 |
| 12 | $RuO_2$—$4MnCO_3$ | $Bu_4PBr$ | 85.8 | 2.3 | | 1.2 | 0.6 | | 1.6 | 86 |

TABLE I-continued

METHANOL-RICH ALKANOLS FROM SYNGAS[a]

| Example | Catalyst Composition | Melt | \multicolumn{7}{c}{LIQUID PRODUCT COMPOSITION (WT %)[d]} | Liquid Yield Increase (Wt %) |
|---------|----------------------|------|------|------|------|-------|-------|---------|------|------|
|         |                      |      | MeOH | EtOH | PrOH | MeOAc | EtOAc | CH$_3$CHO | H$_2$O | |
| 13 | Mn$_2$(CO)$_{10}$ | Bu$_4$PBr[b] | — | — | — | — | — | — | — | F5 |

[a]Typical operating conditions: Ru, 2 mmole; Bu$_4$PBr, 29.7 mmole; 220° C.; 6350 psig; CO/H$_2$(1:1); 6 hours.
[b]Run time; 18 hours.
[c]Operated at 4000 psig CO/H$_2$ (1:1 molar) initial pressure, variable pressure run.
[d]Analysis via glc and Karl Fischer titration.

EXAMPLE 14

This example illustrates another ruthenium-manganese catalyst combination.

A mixture of ruthenium(IV) oxide (2 mmoles) and manganese(II) carbonate (16 mmoles) dispersed in tetrabutylphosphonium bromide (10.0 g) was transferred in a glass liner under N$_2$ purge, to an 850 ml capacity pressure reactor equipped with heating and means of agitation. The reactor was sealed, flushed with a mixture of carbon monoxide and hydrogen (1:1 molar) and pressured to 2000 psig with the carbon monoxide-hydrogen mixture. The mixture was heated to 220° C. with rocking, the pressure raised to 6000 psig by addition of the carbon-monoxide-hydrogen mixture from a large surge tank, and the reactor held at temperature for 6 hours. Pressure in the reactor was maintained at ca. 6000 psig by incremental additions of the carbon monoxide-hydrogen mixture from the surge tank.

On cooling, the reactor pressure (3925 psig) was noted, a typical gas sample taken, and the excess gas removed. The burnt orange liquid product (22.6 g) was analyzed by gas liquid chromatography and Karl-Fischer titration and the following results were obtained:

- 86.3 wt. % methanol
- 2.3 wt. % ethanol
- 1.3 wt. % methyl acetate
- 0.5 wt. % ethyl acetate
- 2.0 wt. % water The liquid yield increase was: (22.6−12.2)/12.2×100=85 wt.%

The alkanol and ester product fractions were recovered from the crude liquid product by fractional distillation in vacuo. Distillate fractions showed high alcohol content. The dark-red liquid residue (11.9 g) resolidified upon cooling.

What is claimed is:

1. A process for making alkanols which comprises of contacting a mixture of CO and H$_2$ at a pressure of 500 psig or greater and at a temperature of at least 180° C. with a catalyst system comprising a ruthenium-containing compound and a material selected from the group consisting of a halogen-free rhenium-containing compound and a halogen-free manganese-containing compound, dispersed in a low melting quaternary phosphonium base or salt.

2. The process of claim 1 wherein the process is conducted at a pressure of about 2000 psig to about 9000 psig.

3. The process of claim 1 wherein the process is conducted at a temperature of about 180° to about 250° C.

4. The process of claim 1 wherein the said material is a rhenium-containing compound.

5. The process of claim 1 wherein the said material is a manganese-containing compound.

6. The process of claim 1 wherein said quaternary salt or base has a melting point less than about 180° C.

7. The process of claim 1 wherein said quaternary salt is a tetraalkylphosphonium salt.

8. The process of claim 7 wherein said alkyl groups contain 1-6 carbon atoms.

9. The process of claim 1 wherein said quaternary is a mixed alkylaryl phosphonium quaternary.

10. The process of claim 1 wherein said quaternary salt is tetrabutylphosphonium salt.

11. The process of claim 10 wherein said tetrabutylphosphonium salt is selected from the group consisting of tetrabutylphosphonium bromide, tetrabutylphosphonium chloride, tetrabutylphosphonium iodide, tetrabutylphosphonium acetate and tetrabutylphosphonium chromate.

12. The process of claim 1 wherein said quaternary phosphonium base is tetrabutylphosphonium hydroxide.

13. The process of claim 1 wherein the ruthenium-containing compound is selected from the group consisting of one or more oxides of ruthenium, ruthenium complexes of carbonyl-containing ligands, ruthenium salts of an organic carboxylic acid and ruthenium carbonyl and hydrocarbonyl derivatives.

14. The process of claim 1 wherein the ruthenium-containing compound is selected from the group consisting of anhydrous ruthenium(IV) dioxide, ruthenium(IV) dioxide hydrate, ruthenium(VIII) tetraoxide, ruthenium acetate, ruthenium propionate, ruthenium(III) acetylacetonate and triruthenium dodecarbonyl.

15. The process of claim 1 wherein said ruthenium-containing compound is ruthenium(IV) dioxide.

16. The process of claim 1 wherein said ruthenium-containing compound is triruthenium dodecacarbonyl.

17. The process of claim 1 wherein the said metal-containing compound is a rhenium-containing compound selected from the group consisting of rhenium carbonyls, rhenium salts of an organic carboxylic acid, and rhenium complexes with carbonyl-containing ligands.

18. The process of claim 1 wherein the phenium-containing compound is selected from the group consisting of rhenium carbonate, rhenium acetylacetonate and dirhenium decacarbonyl.

19. The process of claim 1 wherein the rhenium-containing compound is dirhenium decacarbonyl.

20. The process of claim 1 wherein the said metal-containing compound is a manganese-containing compound selected from the group consisting of one or more manganese carbonates, manganese complexes of carbonyl-containing ligands, manganese carbonyls and manganese salts of organic acids.

21. The process of claim 1 wherein the manganese-containing compound is selected from the group consisting of manganese(II) carbonate, manganese(III) acetylacetonate, manganese acetate and dimanganese decacarbonyl.

22. The process of claim 1 wherein the manganese-containing compound is manganese(II) carbonate.

23. The process of claim 1 wherein the manganese-containing compound is dimanganese decacarbonyl.

* * * * *